United States Patent [19]

Gunselman

[11] Patent Number: 4,674,629
[45] Date of Patent: Jun. 23, 1987

[54] SUTURE CARRIER

[75] Inventor: Robert A. Gunselman, Ephrata, Pa.

[73] Assignee: Sharpoint, Inc., Reading, Pa.

[21] Appl. No.: 807,325

[22] Filed: Dec. 10, 1985

[51] Int. Cl.⁴ .................. A61L 17/06; B65D 85/24
[52] U.S. Cl. ........................... 206/63.3; 206/227;
206/339; 206/382; 206/523
[58] Field of Search .............. 206/63.3, 338, 339,
206/382, 383, 227, 523

[56] References Cited

U.S. PATENT DOCUMENTS

| | | | |
|---|---|---|---|
| 1,887,529 | 11/1932 | Themak | 206/63.3 |
| 3,951,261 | 4/1976 | Mandel et al. | 206/227 |
| 3,985,227 | 10/1976 | Thyen et al. | 206/63.3 |
| 4,120,395 | 10/1978 | Mandel et al. | 206/63.3 |
| 4,183,431 | 1/1980 | Schmidt et al. | 206/63.3 |
| 4,287,987 | 9/1981 | Hoffman et al. | 206/63.3 |
| 4,533,041 | 8/1985 | Aday et al. | 206/63.3 |
| 4,549,649 | 10/1985 | Roshdy | 206/63.3 |

*Primary Examiner*—William Price
*Assistant Examiner*—Brenda J. Ehrhardt
*Attorney, Agent, or Firm*—William H. Elliott, Jr.; Richard D. Weber

[57] ABSTRACT

A carrier for armed sutures comprises a flat elongated card of foam material shaped to form a body portion, neck portion and head portion. A shaped cut adjacent the neck portion of the card permits the separation of the head portion for utilization as a needle park.

7 Claims, 3 Drawing Figures

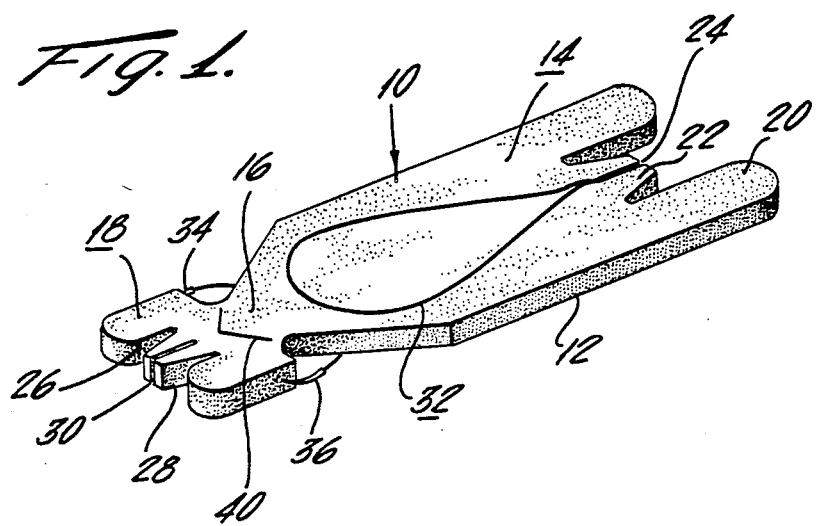
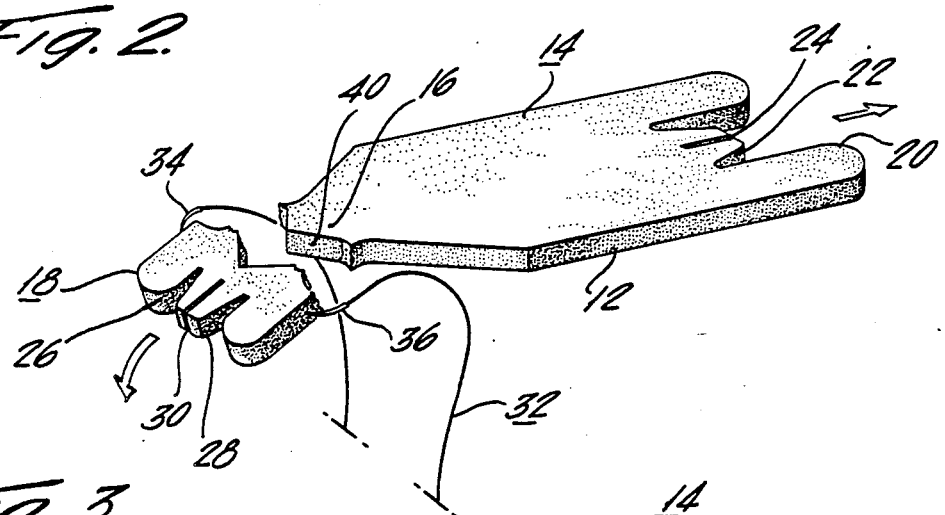
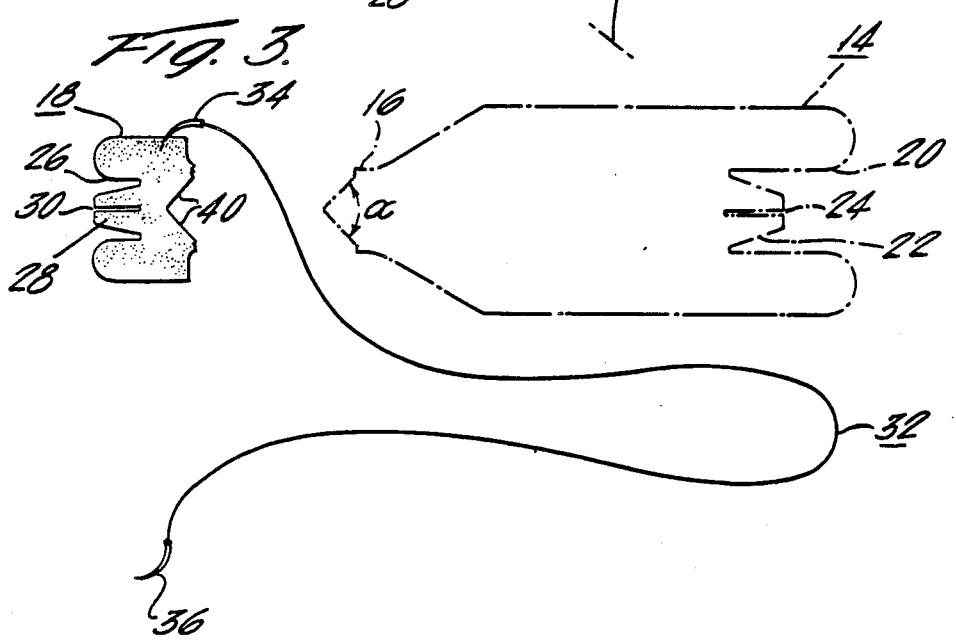

SUTURE CARRIER

FIELD OF THE INVENTION

The present invention relates generally to the packaging of surgical supplies and relates more particularly to carriers for armed sutures.

BACKGROUND OF THE INVENTION

Suppliers of surgical suture threads commonly supply such threads with needles secured to the thread. This is especially the case for needles of relatively smaller sizes, such as those used in ophthalmic, neurologic, plastic and reconstruction, vascular and microsurgery. The convention that is adopted in this specification is to refer to the combined unit of the needle and surgical thread as a "suture". Such sutures can be "single-armed" (i.e., having a needle attached to one end of the ligature) or "double-armed" (i.e., having a needle attached to each end of the thread).

In order to facilitate use of the suture by the surgeon and prevent the cutting edges or points of the needles from becoming damaged, and the threads from becoming kinked, knotted or tangled, many different types of packages have been conceived for surgical sutures. In some of these designs, the sharp points of needles are received in a small block of pierceable material and the ligature is either wound about or folded within portions of the package. Examples of such packages are shown in U.S. Pat. Nos. 3,951,261, 3,985,227 and 4,120,395. In these designs, a small block of pierceable material is used to hold the needle and this small piece can become dislodged from its holder and be lost. Also, with packages of this type, the ligatures tend to become tangled.

Other forms of suture packages employing blocks of pierceable material to hold and protect sutures are shown in U.S. Pat. No. 4,183,431.

To overcome the above disadvantages, suture packages utilizing a relatively large, flat body of a pierceable, nonsloughing foam material have been proposed and used, such as that shown in U.S. Pat. No. 4,287,987. In one variation of such package, the holder comprises an elongated generally rectangular foam block having a portion of reduced width at one end thereof to receive the needle or needles, the thread being wrapped about the central portion of the holder. Although such large suture carriers are excellent for packaging and storage of the sutures, they are bulky and cumbersome to use during surgical procedures. There can be difficulties in removing the suture from the carrier, and the carrier is usually too large to conveniently serve as a needle park to protect and locate a needle when it is temporarily set aside. The park can prevent snagging of the needle in surgical drapes and consequent pull-off of the needle from the suture thread.

SUMMARY OF THE INVENTION

The present invention comprises a suture carrier card of an elongated shape having a body portion, a neck portion and a head portion. A single or double armed suture is disposed on the card with the needle or needles thereof partially embedded in the head portion of the card and with the remainder of the suture wound longitudinally around the card. A shaped cut in the card extending partway across the neck portion thereof and symmetrically disposed with respect to the longitudinal card axis permits the ready separation of the head portion from the remainder of the card to facilitate the preparation of the suture for the surgical procedure and to permit the utilization of the head portion as a needle park during a procedure. The shaped cut aids in maintaining the rigidity of the carrier at times when the suture is being mounted on or removed from the carrier. This is important for ease of use during manufacture and when the suture is being removed for use.

It is accordingly a first object of the invention to provide an improved carrier for armed sutures, a portion which may be detached to serve as a needle park.

Another object of the invention is to provide a suture carrier as described from which the suture may be quickly removed in preparation for a surgical procedure.

A further object of the invention is to provide a needle carrier as described which provides the option of a second needle park should such be required.

Another object of the invention as to provide a carrier as described of a relatively simple structure which can be easily and economically manufactured.

Additional objects and advantages of the invention will be more readily apparent from the following detailed description of a preferred embodiment thereof.

BRIEF DESCRIPTION OF THE DRAWINGS

FIG. 1 is a perspective view of a suture carrier in accordance with the invention showing a double armed suture in its packaged position on the carrier;

FIG. 2 is a perspective view of the carrier and armed suture of FIG. 1 showing the head portion of the carrier after its separation from the carrier body portion and with the suture being withdrawn from the carrier body portion; and FIG. 3 is a plan view showing the carrier head portion serving as a needle park for one of the suture needles, the body portion of the carrier being shown in dot/dash lines.

DESCRIPTION OF THE PREFERRED EMBODIMENT

Referring to the drawings and particularly FIG. 1 thereof, a carrier generally designated 10 for armed sutures comprises a flat, elongated card 12 which is preferably made of a closed-cell foam material. The card 12 is generally symmetrical along its longitudinal axis and includes a large body portion 14 which narrows at one end thereof into a neck portion 16 from which extends a small head portion 18.

The free ends of both the body portion 14 and the head portion 18 include means for facilitating the winding of sutures of various lengths longitudinally around the card. A slot 20 of a modified W-shape in the body portion 14 creates a nose portion 22 through which a longitudinal slit 24 is cut for receiving a suture. Similarly, the head portion 18 includes a W-shaped slot 26 forming a similar nose portion 28 through which a longitudinal slit 30 is cut to secure a packaged suture.

In the embodiment illustrated, a double armed suture 32 is shown including swaged needles 34 and 36 which are partially embedded in the opposite side walls of the head portion 18 of the card. The suture extends from the needles beneath the card and passes through the slit 24 in the body portion nose 22 with the loop portion of the suture resting on the upper surface of the card body portion as shown in FIG. 1. Should a longer suture be involved, it may be passed through the slit 30 in the nose portion 28. The carrier with the suture thus attached may then be sterily packaged in a transparent blister type container in a conventional manner.

The material from which the card 12 is made should be sufficiently soft so as to be readily pierceable by the needles without damaging the needle cutting edges and be sufficiently strong and resilient to hold the needles in place even after repeated insertions and removals. The material furthermore should not crumble or release debris upon removal of the needles since any debris released might become attached to a needle. The material must have sufficient rigidity to remain in a substantially planar condition so as to maintain the integrity of the package until the package is opened.

A preferred closed-cell foam for this purpose is a polyethylene foam sold under the trademark "VOLARA" by Voltek. Foam having a density of about two lbs./ft.$^3$ to four lbs./ft.$^3$ are preferable.

The card 12 should have a sufficient thickness to permit the ready insertion of the needle point into the side walls thereof in the manner shown in FIG. 1. This thickness may vary depending upon the size of the needles and suture.

The carrier details thus far described are essentially conventional. The improvement of the present invention is directed to a means permitting separation of the head portion of the carrier card from the body portion thereof so that the head portion may be utilized as a needle park as shown for example in FIG. 3. This means comprises a shaped cut 40 passing through the card in the neck portion of the card. As shown in the drawings, the cut 40 preferably has a V-shape and is symmetrically disposed with respect to the longitudinal axis of the card with the ends thereof extending toward and closely spaced from the side walls of the narrowest region of the card neck portion 16.

For separation of the head portion from the remainder of the card, as shown in FIG. 2 the head portion is simply pulled longitudinally away from the main body or rotated downwardly or upwardly to tear the connecting portions of the card at each end of the cut 40 thereby freeing the head portion 18 and allowing the head portion, with or without a suture mounted on it, to be retained and the remainder of the card may then be discarded. It should be noted that prior to such separation, the suture thread has been unwound from the body portion of the card. As shown in FIG. 3, one needle 34 may reside in the head portion 18 while the other needle 36 is manipulated by means of a needle holder (not shown) in a surgical procedure, for example in generating a running suture. The needle which is not being used is thus protected and can be readily located at such time as it is needed. The lodging of the needle in the needle park further facilitates the arming of the needle holder, particularly with the extremely small needles used with microsutures. In those situations in which a second needle park is required, the remainder of the card following removal of the head portion may also be employed as a needle park.

The shape of the cut 40 is preferably a V-shape as illustrated, but other cut shapes could also be employed without compromising the integrity of the card. For example, the cut could comprise a pair of connected V-cuts, essentially a W, or as another example, an S-shaped cut symmetrically disposed with respect to the card longitudinal axis. The cut could, in fact, comprise shapes that provide a significant "notching effect" that resists rotation of the head portion about an axis defined by the two ends of the cut. The cut might appropriately be referred to as a "non-linear" cut.

The V-shaped cut has been found to produce the maximum retention of overall card stiffness yet provide the desired ease of removal. It has further been found that V-shapes having apex angles α between 80° and 120° yield acceptable combinations of stiffness and removal ease, with an apex angle of about 100° to 105° yielding the optimum combination of these factors. In fact, it has been found that the cut 40 can extend across 75% of the width of neck portion 16, yet the head portion will remain stable and resist bending with respect to the remainder of the card.

Manifestly, changes in details of construction can be effected by those skilled in the art without departing from the invention.

I claim:

1. A suture carrier comprising a flat elongated card of foam material, including means at one end thereof for receiving a length of suture material, a region of reduced width of said card adjacent one end thereof adapted to receive a needle or needles of a suture carried by the card, a non-linear shaped cut extending transversely across the reduced width region of said card from a point closely spaced from one side edge thereof to a point closely spaced from the opposite edge thereof, said shaped cut permitting the separation of said reduced width portion of the card from the remainder thereof to facilitate removal of the suture from the card and permit utilization of the separated reduced width portion as a needle park, said shaped cut prior to such separation providing the requisite card stability and stiffness to permit handling of the card during suture attachment and removal.

2. The invention as claimed in claim 1, wherein said shaped cut comprises a substantially V-shaped cut disposed symmetrically with respect to the longitudinal axis of said card.

3. The invention as claimed in claim 2 wherein the apex angle of said V-shaped cut is within the range of 80° to 120°.

4. A suture carrier comprising a flat elongated card of closed-cell foam material, said card comprising a body portion, a neck portion of reduced width, and a head portion substantially smaller than said body portion, means at at least one end of said card for receiving a length of suture wrapped longitudinally around said end of said card, said card having a sufficient thickness to permit the penetration and storage of a suture needle in the side edge of the head portion thereof, a non-linear shaped cut in said card neck region extending from a point near one side edge of said neck portion to a point near the opposite side edge of said neck portion, said shaped cut permitting the separation of said head portion from the remainder of said card to facilitate removal of the sutrue from the card and to permit utilization of said head portion as a needle park, said shaped cut prior to such separation providing the requisite card stability and stiffness to permit handling of the card during suture attachment and removal.

5. The invention as claimed in claim 4, wherein said shaped cut extends across said card neck portion at the narrowest portion of said neck portion.

6. The invention as claimed in claim 4, wherein said shaped cut comprises a substantially V-shaped cut disposed symmetrically about the longitudinal axis of said card.

7. The invention as claimed in claim 6 wherein the apex angle of said V-shaped cut is within the range of 80° to 120°.

* * * * *